United States Patent
Gan et al.

(10) Patent No.: US 12,428,667 B2
(45) Date of Patent: Sep. 30, 2025

(54) METHOD FOR LIGATING NUCLEIC ACID FRAGMENTS, METHOD FOR CONSTRUCTING SEQUENCING LIBRARY, AND USE

(71) Applicant: GeneMind Biosciences Company Limited, Shenzhen (CN)

(72) Inventors: Guangli Gan, Shenzhen (CN); Qunting Lin, Shenzhen (CN); Yunyang Cheng, Shenzhen (CN); Meng Zhang, Shenzhen (CN); Gailing Li, Shenzhen (CN); Qin Yan, Shenzhen (CN); Luyang Zhao, Shenzhen (CN)

(73) Assignee: GeneMind Biosciences Company Limited, Shenzhen (CN)

( * ) Notice: Subject to any disclaimer, the term of this patent is extended or adjusted under 35 U.S.C. 154(b) by 1177 days.

(21) Appl. No.: 17/266,542

(22) PCT Filed: Aug. 6, 2019

(86) PCT No.: PCT/CN2019/099360
§ 371 (c)(1),
(2) Date: Feb. 5, 2021

(87) PCT Pub. No.: WO2020/029941
PCT Pub. Date: Feb. 13, 2020

(65) Prior Publication Data
US 2021/0317507 A1    Oct. 14, 2021

(30) Foreign Application Priority Data
Aug. 7, 2018 (CN) .......................... 201810890245.4

(51) Int. Cl.
*C12Q 1/6806* (2018.01)
*C12Q 1/6869* (2018.01)

(52) U.S. Cl.
CPC .......... *C12Q 1/6806* (2013.01); *C12Q 1/6869* (2013.01)

(58) Field of Classification Search
CPC .... C12Q 1/6806; C12Q 1/6869; C40B 40/06; C40B 50/06
See application file for complete search history.

(56) References Cited

U.S. PATENT DOCUMENTS

| | | |
|---|---|---|
| 2003/0186301 A1 | 10/2003 | Christian et al. |
| 2012/0283144 A1 | 11/2012 | Kucera et al. |
| 2018/0216177 A1 | 8/2018 | Zwirko et al. |

FOREIGN PATENT DOCUMENTS

| | | | |
|---|---|---|---|
| CN | 102296065 A | 12/2011 | |
| CN | 111560651 B | 9/2021 | |
| WO | 2010/048605 A1 | 4/2010 | |
| WO | 2013/017861 A2 | 2/2013 | |
| WO | 2013/104106 A1 | 7/2013 | |
| WO | 2016/170147 A1 | 10/2016 | |
| WO | WO-2017112666 A1 * | 6/2017 | ............. C07H 21/00 |
| WO | 2021/090231 A2 | 5/2021 | |

OTHER PUBLICATIONS

Zhelkovsky et al., Simple and efficient synthesis of 5' pre-adenylated DNA using thermostable RNA ligase, 2011, Nucleic Acids Research, vol. 39, No. 17 (Year: 2011).*
Vandenbroucke et al. ("Quantification of splice variants using real-time PCR." Nucleic acids research 29.13 (2001): 7 pages). (Year: 2001).*
Podnar et al., "Next-Generation Sequencing Fragment Library Construction," *Current Protocols in Molecular Biology* 107(7): 16 pages, 2014.
Belaghzal et al., "Hi-C 2.0: An optimized Hi-C procedure for high-resolution genome-wide mapping of chromosome conformation," *Methods* 123:56-65, 2017.
Chinese Office Action, mailed Dec. 31, 2021, for Chinese Application No. 201810890245.4, 10 pages. (with English Translation).
"2. DNA ligase and T-DNA ligase," Bioengineering for Biopharmaceuticals and Microbial Pharmaceuticals, pp. 10-11, 1995 (with English Machine Translation) (3 pages).
"2.3 Ligase," DNA Cloning Technology, pp. 24-26, 1992 (with English Machine Translation) (5 pages).
"3. DNA Ligase," Plant Genetic Engineering, pp. 23-24, 2006 (with English Machine Translation) (4 pages).
"5.2 DNA and RNA ligase," Molecular Biology Experimental Principles and Techniques, pp. 71-73, 2003 (with English Machine Translation) (7 pages).
"7.5 In vitro connection of DNA molecules," Current Protocols for Molecular Biology, Second Edition, pp. 256-259, 1999 (with English Machine Translation) (9 pages).
Li et al., "Stand-Alone Rolling Circle Amplification Combined with Capillary Electrophoresis for Specific Detection of Small RNA," *Anal. Chem.* 81:4906-4913, 2009.
Zhelkovsky et al., "Simple and efficient synthesis of 5' pre-adenylated DNA using thermostable RNA ligase," *Nucleic Acids Research* 39(17):e117, 2011 (6 pages).

* cited by examiner

*Primary Examiner* — Sahana S Kaup
(74) *Attorney, Agent, or Firm* — Seed IP Law Group LLP (57) ABSTRACT

Disclosed are a method for ligating nucleic acid fragments, a method for constructing a sequencing library, and the use thereof. The method for ligating nucleic acid fragments comprises ligating a first nucleic acid fragment and a second nucleic acid fragment in a mixed enzyme reaction system comprising a DNA ligase and a RNA ligase, wherein the first nucleic acid fragment is double-stranded DNA. The ligation efficiency of the method for ligating nucleic acid fragments can reach 85% or more, and by using this ligation method to construct a sequencing library, the yield of the effective library is significantly improved.

10 Claims, 4 Drawing Sheets

Specification includes a Sequence Listing.

METHOD FOR LIGATING NUCLEIC ACID FRAGMENTS, METHOD FOR CONSTRUCTING SEQUENCING LIBRARY, AND USE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 260085_411USPC_Sequence_Listing.txt. The text file is 2 KB, and is being submitted electronically via EFS-Web.

TECHNICAL FIELD

The present disclosure relates to the technical field of biology, and in particular to a method for nucleic acid fragment ligation, a method for constructing a sequencing library and application thereof.

BACKGROUND

With the development of sequencing technologies, sequencing libraries are widely used. In genetic engineering, it is often necessary to ligate two or more nucleic acid fragments, for example, ligating an adapter, typically a short blunt-ended or sticky-ended synthetic oligonucleotide fragment, to a DNA molecule. The ligation efficiency between the adapter and nucleic acids directly affects the quality of the constructed sequencing library.

SUMMARY

The present disclosure provides a method for nucleic acid fragment ligation, which is easy to operate and high in efficiency. Also provided is a method for constructing a sequencing library and application thereof in sequencing.

In one aspect, the present disclosure provides a method for nucleic acid fragment ligation, comprising: ligating a first nucleic acid fragment and a second nucleic acid fragment in a mixed enzyme reaction system comprising a DNA ligase and an RNA ligase, wherein the first nucleic acid fragment is a double-stranded DNA.

In one embodiment, the RNA ligase is T4 RNA ligase; and/or the DNA ligase is a DNA ligase which can catalyze the ligation of sticky-ended or blunt-ended double-stranded DNA, for example T4 DNA ligase and/or Blunt/TA ligase.

In one embodiment, the first nucleic acid fragment is a phosphorylated nucleic acid fragment.

In one embodiment, the phosphorylation is performed using a polynucleotide kinase.

In one embodiment, the polynucleotide kinase is T4 polynucleotide kinase.

In one embodiment, the mixed enzyme reaction system further comprises a polynucleotide kinase.

In one embodiment, the polynucleotide kinase is T4 polynucleotide kinase.

In one embodiment, the second nucleic acid fragment is a double-stranded nucleic acid fragment.

In one embodiment, the molar ratio of the first nucleic acid fragment to the second nucleic acid fragment is 1:8 to 1:20.

In one embodiment, the molar ratio of the first nucleic acid fragment to the second nucleic acid fragment is 1:10.

In one embodiment, the final concentration of the RNA ligase in the ligation reaction system is 0.15 U/µL to 1 U/µL; and/or the final concentration of the polynucleotide kinase in the phosphorylation system is 0.3 U/µL to 1 U/µL.

In another aspect, the present disclosure provides a method for constructing a sequencing library, comprising acquiring a ligation product by the method for ligation of any of the above embodiments to obtain a sequencing library, the first nucleic acid fragment comes from a sample under test.

In a third aspect, the present disclosure provides a sequencing library given by the library construction method of any of the above embodiments.

In a fourth aspect, the present disclosure provides a method for sequencing, comprising sequencing the sequencing library obtained by the method of any of the above embodiments.

In a fifth aspect, the present disclosure provides a kit for implementing the method of any of the above embodiments.

RNA ligases are enzymes for RNA ligation. In the method for nucleic acid fragment ligation provided by the present disclosure, the reaction system simultaneously comprises a DNA ligase and an RNA ligase, and surprisingly, the DNA ligation efficiency is obviously improved. The experimental result shows that in a condition without RNA ligase where only DNA ligase is used for double-stranded DNA fragment ligation, the ligation efficiency is only 38.14-77.5%; however, when an RNA ligase commonly used for the ligation between RNAs is added, the DNA fragment ligation efficiency reaches more than 85%. When a sequencing library is constructed by this method for ligation, the yield of the effective library is obviously improved.

DETAILED DESCRIPTION

The aforementioned purposes, features and advantages of the present disclosure will be more apparent from the description of the embodiments and drawings below. The following examples are illustrative only and are not to be construed as limiting the present disclosure.

The present application claims priority to Chinese Patent Application No. 201810890245.4, the entirety of which is incorporated herein by reference.

In one aspect, the present disclosure provides a method for nucleic acid fragment ligation, comprising: ligating a first nucleic acid fragment and a second nucleic acid fragment in a mixed enzyme reaction system comprising a DNA ligase and an RNA ligase, wherein the first nucleic acid fragment is a double-stranded DNA.

Specifically, the first nucleic acid fragment may be a DNA fragment derived from cfDNA, genomic DNA, and/or PCR product, and the fragment may be blunt/end-filled or not.

Furthermore, the first nucleic acid fragment is a phosphorylated nucleic acid fragment.

Specifically, the first nucleic acid fragment is phosphorylated using a polynucleotide kinase.

Furthermore, the polynucleotide kinase is T4 polynucleotide kinase.

In one embodiment, the mixed enzyme reaction system further comprises a polynucleotide kinase. The polynucleotide kinase phosphorylates the first nucleic acid fragments in a ligation process in a mixed enzyme system, thereby simplifying the operation and improving efficiency.

Specifically, the polynucleotide kinase in the mixed enzyme system is T4 polynucleotide kinase. The T4 polynucleotide kinase (T4 PNK) can phosphorylate the ends of a double-stranded DNA fragment to form a fragment with phosphate group at the 5' ends.

Specifically, the second nucleic acid fragment is a double-stranded nucleic acid fragment having a known sequence, for example, a adapter. The adapter is a nucleotide fragment of a known sequence.

Furthermore, the adapter comprises a forward strand and a reverse strand, wherein the forward strand has an amino modification at the 5' end and a hydroxyl modification at the 3' end, and the reverse strand has a phosphorylation modification at the 5' end, and a fluorescent label at the 3' end. The 5' end of the reverse strand can be ligated to the first nucleic acid fragment, and the forward and reverse strands forming the double-stranded adapter.

Further, the adapter may be a blunt-ended adapter, a sticky-ended adapter, or the like.

Specifically, the fluorescent label may be a detectable fluorescent label such as CY3, TRITC or TAMRA.

In one embodiment, the RNA ligase is T4 RNA ligase. T4 RNA ligase is commonly used for the ligation between RNAs, The inventor surprisingly found that when T4 RNA Ligase is used in the ligation between a double-stranded DNA and a adapter, it works well with T4 PNK and T4 DNA ligase, achieving a ligation efficiency over 85% and a high yield of effective library.

Furthermore, the DNA ligase may be T4 DNA ligase and/or Blunt/TA ligase, etc., for ligating blunt-ended or sticky-ended DNAs.

In this embodiment, the DNA ligase is T4 DNA ligase which catalyzes the formation of phosphodiester bonds between adjacent 3' hydroxyl and 5' phosphate ends on the double-stranded DNA and facilitates the ligation of the double-stranded DNA fragment to the adapter.

In one embodiment, the first nucleic acid fragment is a phosphorylated nucleic acid fragment.

In one embodiment, the phosphorylation is performed using a polynucleotide kinase.

In one embodiment, the molar ratio of the first nucleic acid fragment to the second nucleic acid fragment is 1:8 to 1:20. The molar ratio of the first nucleic acid fragment to the second nucleic acid fragment is appropriate for reducing the residue of the second nucleic acid fragment effectively.

Furthermore, the molar ratio of the first nucleic acid fragment to the second nucleic acid fragment is 1:10.

In one embodiment, the final concentration of the RNA ligase in the ligation reaction system is 0.15 U/μL to 1 U/μL; and/or Furthermore, the final concentration of the polynucleotide kinase in the phosphorylation system is 0.3 U/μL to 1 U/μL.

In this embodiment, the ligation of the double-stranded DNA and the adapter specifically comprises the following steps: incubating the double-stranded DNA fragment in a mixed enzyme reaction system comprising T4 polynucleotide kinase (T4 PNK), T4 DNA ligase and T4 RNA ligase for ligation, and co-incubating the double-stranded DNA fragment and the adapter for ligation to give a ligation product.

Specifically, DNA may be fragmented by restriction enzymes, mechanical disruption, or the like, to form DNA fragments of appropriate length to facilitate ligation of the DNA fragments to the adapters. Certainly, if the length of the double-stranded DNA itself is within the appropriate length range or smaller than the appropriate length, the fragmentation is not required. The appropriate length may vary based on the sequencing platform. Before the randomly fragmented DNA fragments are ligated to the adapter, a filling-in treatment is usually performed, or the filling-in and ligation are performed simultaneously under the action of DNA ligase. However, for the present disclosure, the reaction system is suitable for the ligation of randomly fragmented DNA fragments without the filling-in process. Preferably, the T4 RNA ligase used is T4 RNA ligase I.

In one embodiment, the ligation reaction is conducted in a two-step process as follows: incubating the double-stranded DNA fragment in a mixed enzyme system consisting of T4 polynucleotide kinase and T4 DNA ligase buffer for reaction for 20-40 min at 35-40° C. to give an intermediate product, the ends of the double-stranded DNA fragment being modified by phosphorylating with T4 polynucleotide kinase (T4 PNK); and co-incubating the intermediate product and the adapter in a mixed enzyme system consisting of T4 DNA ligase, T4 RNA ligase and T4 DNA ligase buffer for 20-40 min at 10-20° C. to give a ligation product.

In another embodiment, the ligation reaction is conducted in a one-step process as follows: co-incubating the double-stranded DNA fragment and the adapter in a reaction system consisting of T4 polynucleotide kinase, T4 DNA ligase, T4 RNA ligase and T4 DNA ligase buffer for 20-40 min at 10-20° C. to give a ligation product. The one-step process has similar ligation efficiency to the two-step process, but is easy to operate.

Specifically, the molar ratio of the double-stranded DNA fragment to the adapter is 1:8-1:20. The molar ratio of the double-stranded DNA fragment to the adapter is appropriate for reducing the adapter residue effectively.

Furthermore, the molar ratio of the double-stranded DNA fragment to the adapter is 1:10. As such, the amount of the adapter residue is minimized.

In the above method for ligation, an RNA ligase commonly used for ligating RNAs is added. The ligation efficiency of the double-stranded DNA fragments is improved by the cooperation of DNA ligase and RNA ligase. When the method for ligation is used for constructing a sequencing library, the effective library yield is elevated.

In another aspect, the present disclosure provides a method for constructing a sequencing library, comprising acquiring a ligation product by the method for ligation of any of the above embodiments to obtain a sequencing library, the first nucleic acid fragment comes from a sample under test.

The method for constructing a sequencing library features the advantages of convenience, cost-efficiency and high yield of effective library.

In a third aspect, the present disclosure provides a sequencing library obtained by the method for construction of any of the above embodiments. In a fourth aspect, the present disclosure provides a method for sequencing, comprising performing a sequencing procedure on the sequencing library obtained by the method of any of the above embodiments.

In a fifth aspect, the present disclosure provides a kit for implementing the method of any of the above embodiments.

For example, the kit comprises a DNA ligase, an RNA ligase, and a package insert of the kit describing the method for ligation.

In one embodiment, the kit comprises a DNA ligase and an RNA ligase stored in the form of mixed enzymes.

In one embodiment, the kit further comprises an adapter.

The kit according to any of the above embodiments can be used to implement the efficient ligation of DNA fragments.

In the following examples, unless otherwise stated, the procedures without specifying the specific conditions are usually conducted according to conventional conditions, for example, see the *Molecular Cloning: A Laboratory Manual* [M] (Beijing Scientific Press, 1992) by Sambuque, E F Friedel, T Mannich, et al. (translated by Jin Dongyan, Li Mengfeng, et. al.) or the method recommended by the kit manufacturer. The reagents or instruments not provided with manufacturer are conventional and commercially available products. As used herein, the term "and/or" includes any and all combinations of one or more of the associated listed items.

In the following examples:

T4 Polynucleotide kinase (T4 PNK) was purchased from NEB, Cat. #M0201S, 10,000 U/mL.

T4 DNA ligase was purchased from NEB, Cat. #M0202. T4 RNA ligase I was purchased from NEB, Cat. #NEB M0204, 10,000 U/mL. Certainly, in other examples, ligases of other brands, such as Blunt/TA ligase mix of Vazyme Biotech Inc., may be used for ligation.

The synthetic sequences design is as follows:

```
                                         (SEQ ID No. 1)
TCCTTGATACCTGCGACCATCCAGTTCCACTCAGATGTGTATAAGAGAC

AG;

(SEQ ID No. 2)
CTGTCTCTTATACACATCTGAGTGGAACTGGATGGTCGCAGGTATCAAG

GA;

(SEQ ID No. 3)
CTCAGATCCTACAACGACGCTCTACCGATGAAGATGTGTATAAGAGACA

G;
and (SEQ ID No. 4)
CTGTCTCTTATACACATCTTCATCGGTAGAGCGTCGTTGTAGGATCTGAG
```

D9 adapter:

D9-S1 (forward strand): a sequence set forth in SEQ ID No. 1 with a modified amino group (—NH$_2$) at the 5' end;

D9-S2 (reverse strand 1): a sequence set forth in SEQ ID No. 2 with a modified phosphate group (PHO—) at the 5' end and an amino group (—NH$_2$) at the 3' end;

D9-S2-CY3 (reverse strand 2): a sequence set forth in SEQ ID No. 2 with a modified phosphate group (PHO—) at the 5' end and a fluorescent group (—CY3) at the 3' end;

D9-1 adapter: a double-stranded polynucleotide formed by sequences D9-S1 (forward strand) and D9-S2-CY3 (reverse strand 2); and D9-2 adapter: a double-stranded polynucleotide formed by sequences D9-S1 (forward strand) and D9-S2-CY3 (reverse strand 1).

D7 adapter:

D7-S1 (forward strand): a sequence set forth in SEQ ID No. 3 with a modified amino group (—NH$_2$) at the 5' end;

D7-S2 (reverse strand 1): a sequence set forth in SEQ ID No. 4 with a modified phosphate group (PHO—) at the 5' end and an amino group (—NH$_2$) at the 3' end;

D7-S2 (reverse strand 2): a sequence set forth in SEQ ID No. 4 with a modified phosphate group (PHO—) at the 5' end and a fluorescent group (—CY3) at the 3' end;

D7-1 adapter: a double-stranded polynucleotide formed by sequences D7-S1 (forward strand) and D7-S2 (reverse strand 2); and D7-2 adapter: a double-stranded polynucleotide formed by sequences D7-S1 (forward strand) and D7-S2 (reverse strand 1).

Adapter mix (adapter): a mixture of D7-1 adapter and D9-1 adapter in a molar ratio of 1:1.

CY3: CY3 fluorescent dye

The molar ratio of DNA to adapter is the molar ratio of total DNA to adapter mix. In the examples, DNA refers to the PCR product.

D7-2 adapter and D9-2 adapter: the control for ligation product identification by Labchip.

The calculation of the adapter proportion:

Moles of DNA were calculated by the following formula (I):

$$pmols = \frac{m * 10^3}{660 * L}$$

m: weight of DNA fragment added into the system, in ng;

L: length of DNA fragment added into the system, in bp.

Moles of adapter were calculated by the following formula (II):

$$pmols = C * V \qquad (II)$$

C: molar concentration of adapter, in µM;

V: volume of adapter used, in µL.

Moles given by the formula (I) were ratioed against those given by the formula (II) to afford the ratio of DNA to adapter. The ligation efficiency was calculated as follows: the adapter, the substrate and the ligation product were separated by length using capillary electrophoresis on the Labchip platform; and picomoles of DNA with adapter was divided by the sum of picomoles of DNAs and multiplied by one hundred percent to give the ligation efficiency.

Example 1

The method for ligation of the embodiment adopts a two-step process as follows:

15 ng of 200-bp PCR product, 2.5 μL of 10 μM ATP, 1 μL of 10×T4 ligase buffer (containing 10 mM ATP) and 1 μL of T4 PNK were mixed in a 200-μL PCR tube. The mixture was diluted to 10 μL using water, well mixed, and incubated at 37° C. for 30 min to give an intermediate product. 1 μL of 10×T4 ligase buffer, 2 μL of 1 μM adapter mix (adapter; the molar ratio of DNA to adapter was 1:17.6), 1 μL of T4 RNase ligase I and 2 μL of T4 DNA ligase were added to the intermediate product. The mixture was diluted to 20 μL using water, well mixed (the final concentration of T4 RNase ligase I being 0.5 U/μL), and incubated for 30 min at 16° C. to give the ligation product.

Figure 1:
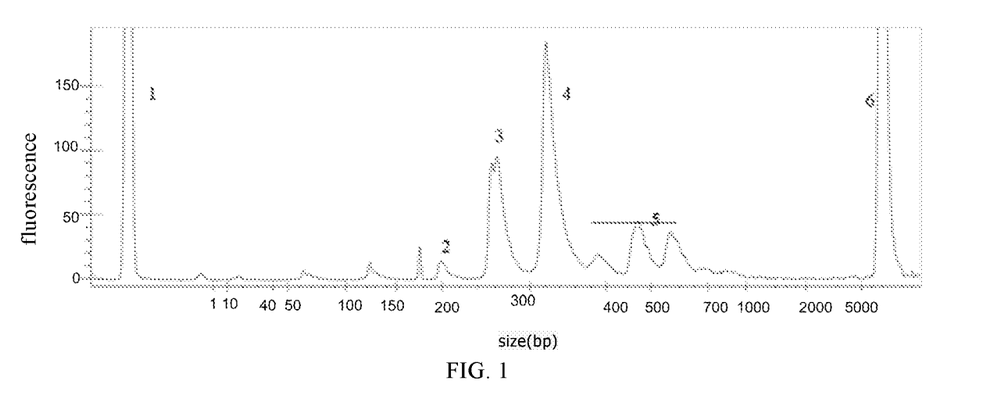
FIG. 1 is a diagram showing the results of identifying the size of ligation product by Labchip in Example 1.

The resulting mixture was purified using 0.8× Ampure XP beads, and was loaded on a Labchip platform to identify the size of ligation product. The results are shown in Table 1 and FIG. 1.

TABLE 1

| No. | Item | Molar concentration (pmol/mL) | % |
|---|---|---|---|
| 1 | Low marker | / | / |
| 2 | 200-bp PCR product | 0.12 | 4.14% |
| 3 | Product with one adapter | 0.95 | 32.76% |
| 4 | Product with two adapters | 1.38 | 47.59% |
| 5 | Polymers with adapter | 0.45 | 15.52% |
| 6 | Up marker | / | / |
| / | Effective library | 2.78 | 95.86% |
| / | Total | 2.9 | / |
| Adapter residue | / | / | 10.5% |

Example 2

The method for ligation of the embodiment adopts a one-step process as follows:

15 ng of 200-bp PCR product, 2 μL of 10×T4 ligase buffer, 2 μL of 1 μM adapter mix (adapter; the molar ratio of DNA to adapter was 1:17.6), 1 μL of T4 PNK, 1 μL of T4 RNase ligase I and 2 μL of T4 DNA ligase were mixed in a 200-μL PCR tube. The mixture was diluted to 20 μL using water, well mixed (the final concentration of T4 RNase ligase I being 0.5 U/μL), and incubated for 1 h at 16° C. to give the ligation product.

Figure 2:
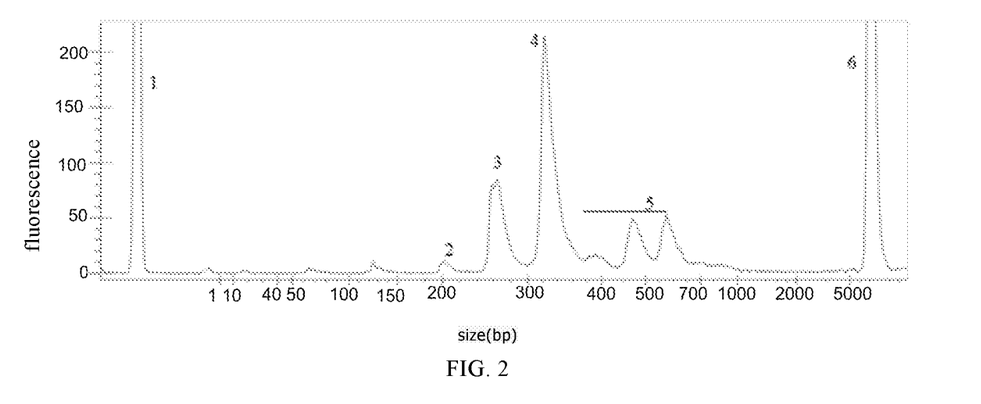
FIG. 2 is a diagram showing the results of identifying the size of ligation product by Labchip in Example 2.

The resulting mixture was purified using 0.8× Ampure XP beads, and was loaded on a Labchip platform to identify the size of ligation product. The results are shown in Table 2 and FIG. 2.

TABLE 2

| No. | Item | Molar concentration (pmol/mL) | % |
|---|---|---|---|
| 1 | Low marker | / | / |
| 2 | 200-bp PCR product | 0.11 | 3.68% |
| 3 | Product with one adapter | 0.84 | 28.09% |
| 4 | Product with two adapters | 1.53 | 51.17% |
| 5 | Polymers with adapter | 0.51 | 17.06% |
| 6 | Up marker | / | / |
| / | Effective library | 2.88 | 96.32% |
| / | Total | 2.99 | / |
| Adapter residue | / | / | 9.10% |

Example 3

The method for ligation of the embodiment adopts a one-step process as follows:

15 ng of 200-bp PCR product, 2 μL of 10×T4 ligase buffer, 2 μL of 1 μM adapter mix (adapter; the molar ratio of DNA to adapter was 1:17.6), 1 μL of T4 PNK, 1 μL of T4 RNase ligase I and 2 μL of T4 DNA ligase were mixed in a 200-4 PCR tube. The mixture was diluted to 20 μL using water, well mixed (the final concentration of T4 RNase ligase I being 0.5 U/μL), and incubated for 1 h at 16° C. to give the ligation product.

Figure 3:
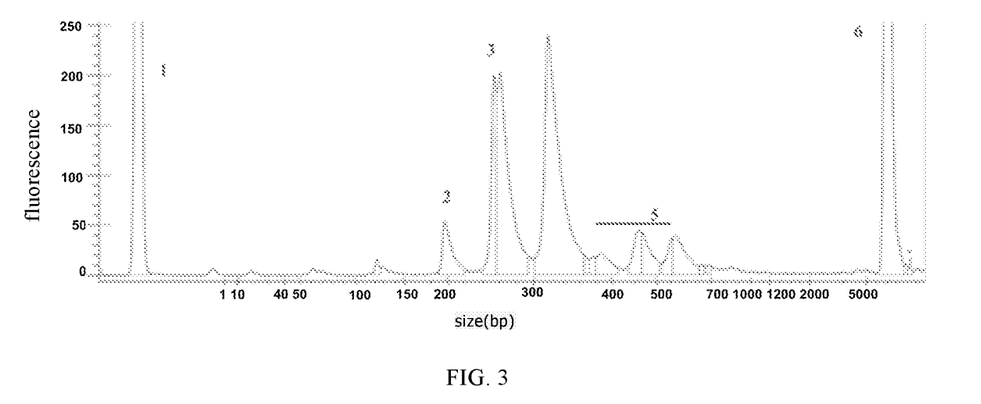
FIG. 3 is a diagram showing the results of identifying the size of ligation product by Labchip in Example 3.

The resulting mixture was purified using 0.8× Ampure XP beads, and was loaded on a Labchip platform to identify the size of ligation product. The results are shown in Table 3 and FIG. 3.

TABLE 3

| No. | Item | Molar concentration (pmol/mL) | % |
|---|---|---|---|
| 1 | Low marker | / | / |
| 2 | 200-bp PCR product | 0.39 | 9.63% |
| 3 | Product with one adapter | 1.74 | 42.96% |
| 4 | Product with two adapters | 1.44 | 35.56% |
| 5 | Polymers with adapter | 0.48 | 11.85% |
| 6 | Up marker | / | / |
| / | Effective library | 3.66 | 90.37% |
| / | Total | 4.05 | / |
| Adapter residue | / | / | 8.8% |

Example 4

The method for ligation of the embodiment adopts a one-step process as follows: The reaction system was prepared in the same manner as in Example 3, except that 1.7 μL of 1 μM adapter mix (adapter) was added was and the molar ratio of DNA to adapter was 1:15. The rest was consistent with Example 3.

Figure 4:
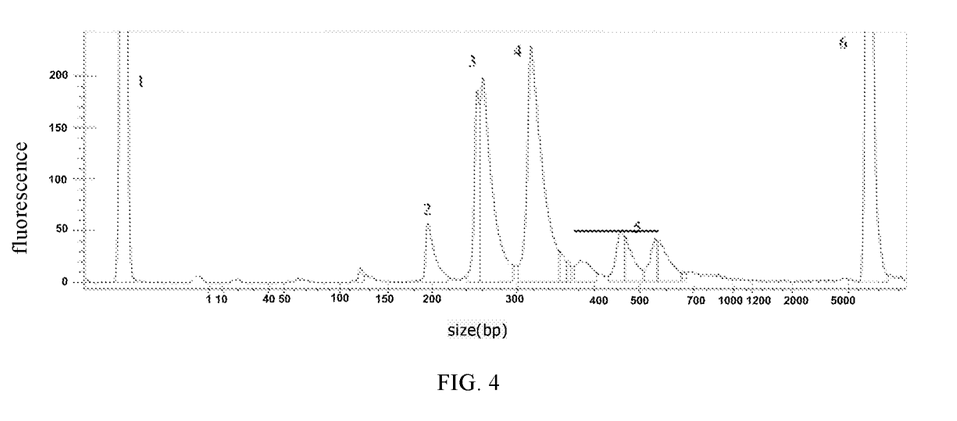
FIG. 4 is a diagram showing the results of identifying the size of ligation product by Labchip in Example 4.

The resulting mixture was purified using 0.8× Ampure XP beads, and was loaded on a Labchip platform to identify the size of ligation product. The results are shown in Table 4 and FIG. 4.

TABLE 4

| No. | Item | Molar concentration (pmol/mL) | % |
|---|---|---|---|
| 1 | Low marker | / | / |
| 2 | 200-bp PCR product | 0.41 | 10.43% |
| 3 | Product with one adapter | 1.65 | 41.98% |
| 4 | Product with two adapters | 1.37 | 34.86% |
| 5 | Polymers with adapter | 0.5 | 12.72% |
| 6 | Up marker | / | / |
| / | Effective library | 3.52 | 89.56% |
| / | Total | 3.93 | / |
| Adapter residue | / | / | 7.9% |

Example 5

The method for ligation of the embodiment adopts a one-step process as follows: The reaction system was prepared in the same manner as in Example 3, except that 1.36 μL of 1 μM adapter mix (adapter) was added and the molar ratio of DNA to adapter was 1:12. The rest was consistent with Example 3.

Figure 5:
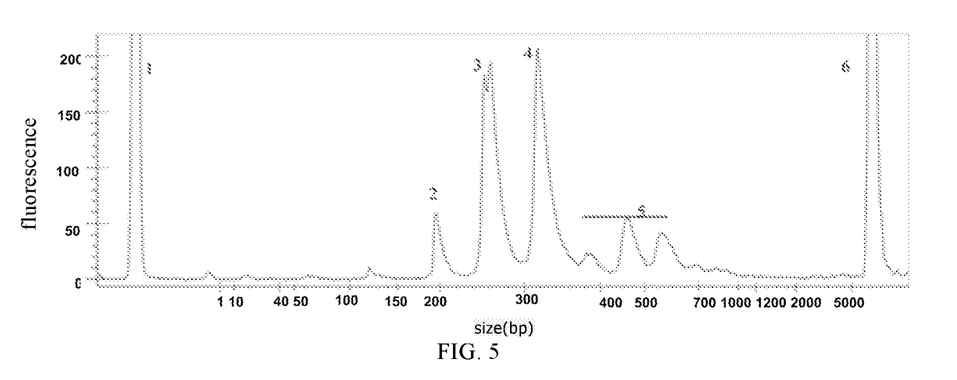
FIG. 5 is a diagram showing the results of identifying the size of ligation product by Labchip in Example 5.

The resulting mixture was purified using 0.8× Ampure XP beads, and was loaded on a Labchip platform to identify the size of ligation product. The results are shown in Table 5 and FIG. 5.

TABLE 5

| No. | Item | Molar concentration (pmol/mL) | % |
|---|---|---|---|
| 1 | Low marker | / | / |
| 2 | 200-bp PCR product | 0.44 | 11.17% |
| 3 | Product with one adapter | 1.68 | 42.64% |
| 4 | Product with two adapters | 1.26 | 31.98 |
| 5 | Polymers with adapter | 0.56 | 14.21% |
| 6 | Up marker | / | / |
| / | Effective library | 3.5 | 88.83% |
| / | Total | 3.94 | / |
| Adapter residue | / | / | 6.4% |

Example 6

The method for ligation of the embodiment adopts a one-step process as follows:

The reaction system was prepared in the same manner as in Example 3, except that 1.14 μL of 1 μM adapter mix (adapter) was added and the molar ratio of DNA to adapter was 1:10. The rest was consistent with Example 3.

Figure 6:
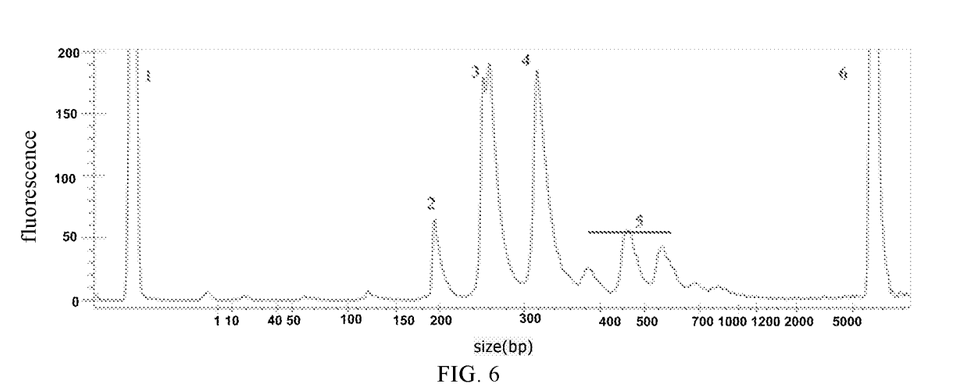
FIG. 6 is a diagram showing the results of identifying the size of ligation product by Labchip in Example 6.

The resulting mixture was purified using 0.8× Ampure XP beads, and was loaded on a Labchip platform to identify the size of ligation product. The results are shown in Table 6 and FIG. 6.

TABLE 6

| No. | Item | Molar concentration (pmol/mL) | % |
|---|---|---|---|
| 1 | Low marker | / | / |
| 2 | 200-bp PCR product | 0.46 | 12.2% |
| 3 | Product with one adapter | 1.62 | 42.97% |
| 4 | Product with two adapters | 1.11 | 29.44% |
| 5 | Polymers with adapter | 0.58 | 15.38% |
| 6 | Up marker | / | / |
| / | Effective library | 3.31 | 87.8% |
| / | Total | 3.77 | / |
| Adapter residue | / | / | 5.53% |

Example 7

The method for ligation of the embodiment adopts a one-step process as follows:

15 ng of 200-bp PCR product, 2 μL of 10×T4 ligase buffer, 1.14 μL of 1 μM adapter mix (adapter; the molar ratio of DNA to adapter was 1:10), 1 μL of T4 PNK, 1 μL of T4 RNase ligase I and 2 μL of T4 DNA ligase were mixed in a 200-μL PCR tube. The mixture was diluted to 20 μL using water, well mixed (the final concentration of T4 RNase ligase I being 0.5 U/μL), and incubated for 30 min at 16° C. to give the ligation product.

Figure 7:
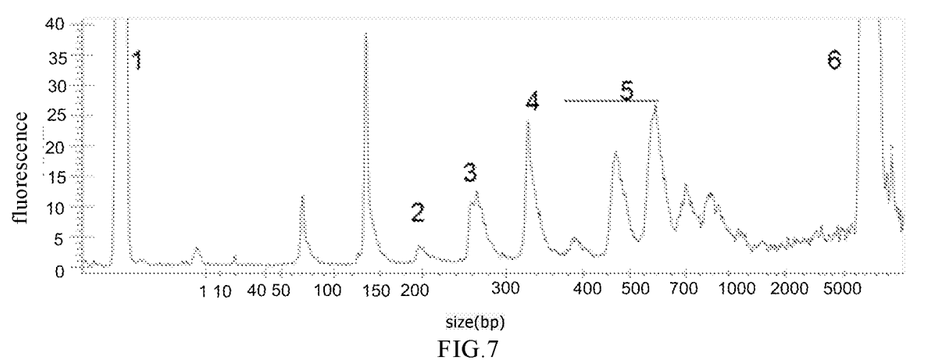
FIG. 7 is a diagram showing the results of identifying the size of ligation product by Labchip in Example 7.

The resulting mixture was purified using 0.8× Ampure XP beads, and was loaded on a Labchip platform to identify the size of ligation product. The results are shown in Table 7 and FIG. 7.

TABLE 7

| No. | Item | Molar concentration (pmol/mL) | % |
|---|---|---|---|
| 1 | Low marker | / | / |
| 2 | 200-bp PCR product | 0.03 | 5.77% |
| 3 | Product with one adapter | 0.11 | 21.15% |
| 4 | Product with two adapters | 0.11 | 21.15% |
| 5 | Polymers with adapter | 0.27 | 51.92% |
| 6 | Up marker | / | / |
| / | Effective library | 0.49 | 94.23% |
| / | Total | 0.52 | / |

Example 8

The method for ligation of the embodiment adopts a one-step process as follows:

The reaction system was prepared in the same manner as in Example 7, except that 1 μL of T4 RNase ligase I and 1 μL of T4 DNA ligase were added. The rest was consistent with Example 7.

Figure 8:
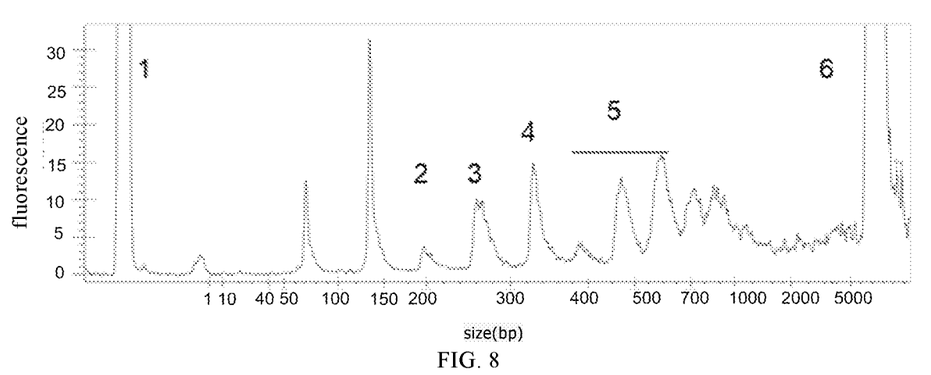
FIG. 8 is a diagram showing the results of identifying the size of ligation product by Labchip in Example 8.

The resulting mixture was purified using 0.8× Ampure XP beads, and was loaded on a Labchip platform to identify the size of ligation product. The results are shown in Table 8 and FIG. 8.

TABLE 8

| No. | Item | Molar concentration (pmol/mL) | % |
|---|---|---|---|
| 1 | Low marker | / | / |
| 2 | 200-bp PCR product | 0.01 | 3.22% |
| 3 | Product with one adapter | 0.07 | 22.58% |
| 4 | Product with two adapters | 0.06 | 19.35% |
| 5 | Polymers with adapter | 0.17 | 54.84% |
| 6 | Up marker | / | / |
| / | Effective library | 0.30 | 96.77% |
| / | Total | 0.31 | / |

Example 9

The method for ligation of the embodiment adopts a one-step process as follows:

The reaction system was prepared in the same manner as in Example 7, except that 0.5 μL of T4 RNase ligase I and 0.5 μL of T4 DNA ligase were added, and the final concentration of T4 RNase ligase I was 0.25 U/μL. The rest was consistent with Example 7.

Figure 9:
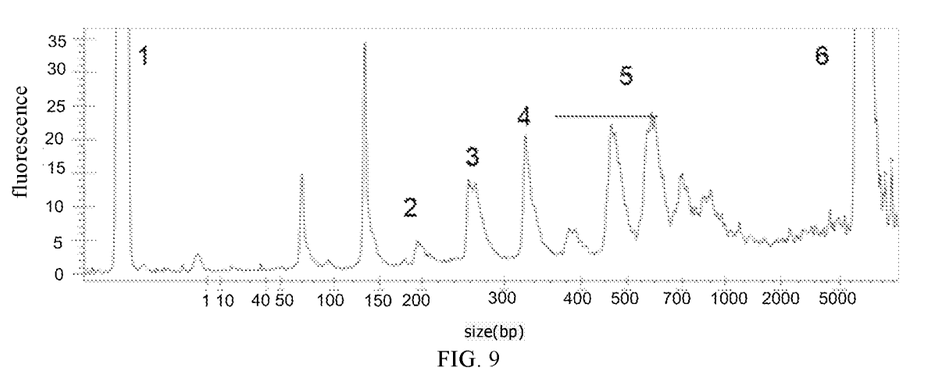
FIG. 9 is a diagram showing the results of identifying the size of ligation product by Labchip in Example 9.

The resulting mixture was purified using 0.8× Ampure XP beads, and was loaded on a Labchip platform to identify the size of ligation product. The results are shown in Table 9 and FIG. 9.

TABLE 9

| No. | Item | Molar concentration (pmol/mL) | % |
|---|---|---|---|
| 1 | Low marker | / | / |
| 2 | 200-bp PCR product | 0.02 | 4.35% |
| 3 | Product with one adapter | 0.11 | 23.91% |
| 4 | Product with two adapters | 0.08 | 17.39% |
| 5 | Polymers with adapter | 0.25 | 54.35% |
| 6 | Up marker | / | / |
| / | Effective library | 0.44 | 95.65% |
| / | Total | 0.46 | / |

Example 10

The method for ligation of the embodiment adopts a one-step process as follows:

ng of 200-bp PCR product, 3 µL of 10×T4 ligase buffer, 1.14 µL of 1 µM adapter mix (adapter; the molar ratio of DNA to adapter was 1:10), 1 µL of T4 PNK, 0.5 µL of T4 RNase ligase I and 0.5 µL of T4 DNA ligase were mixed in a 200-µL PCR tube. The mixture was diluted to 30 µL using water, well mixed (the final concentration of T4 RNase ligase I being 0.17 U/µL), and incubated for 15 min at 16° C. to give the ligation product.

Figure 10:
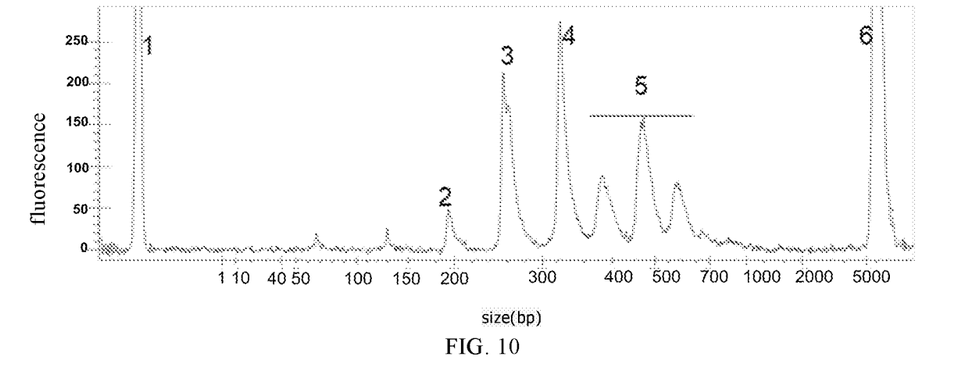
FIG. 10 is a diagram showing the results of identifying the size of ligation product by Labchip in Example 10.

The resulting mixture was purified using 0.8× Ampure XP beads, and was loaded on a Labchip platform to identify the size of ligation product. The results are shown in Table 10 and FIG. 10.

TABLE 10

| No. | Item | Molar concentration (pmol/mL) | % |
|---|---|---|---|
| 1 | Low marker | / | / |
| 2 | 200-bp PCR product | 0.33 | 7.24% |
| 3 | Product with one adapter | 1.51 | 33.11% |
| 4 | Product with two adapters | 1.25 | 27.41% |
| 5 | Polymers with adapter | 1.47 | 32.24% |
| 6 | Up marker | / | / |
| / | Effective library | 4.23 | 92.76% |
| / | Total | 4.56 | / |

Comparative Example 1

The method for ligation of the embodiment adopts a two-step process as follows:

15 ng of 200-bp PCR product, 2.5 µL of 10 µM ATP, 1 µL of 10×T4 ligase buffer and 1 µL of T4 PNK were mixed in a 200-4 PCR tube. The mixture was diluted to 10 µL using water, well mixed, and incubated at 37° C. for 30 min to give an intermediate product. 1 µL of 10×T4 ligase buffer, 2 µL of 1 µM adapter mix (adapter; the molar ratio of DNA to adapter was 1:17.6) and 2 µL of T4 DNA ligase were added to the intermediate product. The mixture was diluted to 20 µL using water, well mixed, and incubated for 30 min at 16° C. to give the ligation product.

Figure 11:
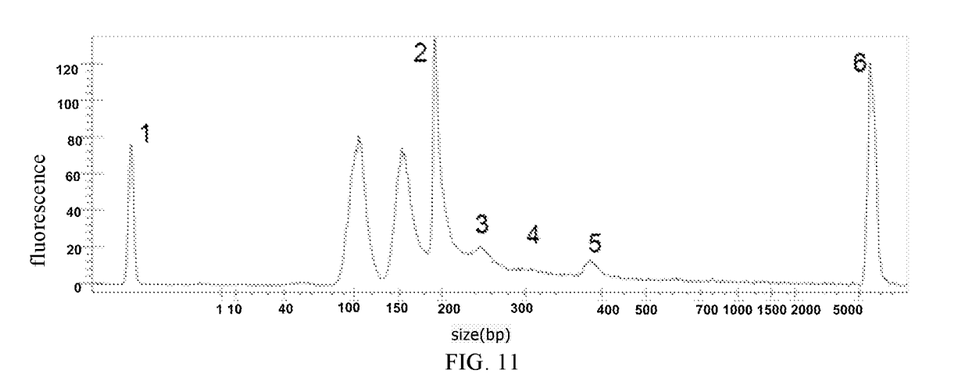
FIG. 11 is a diagram showing the results of identifying the size of ligation product by Labchip in Comparative Example 1.

The resulting mixture was purified using 0.8× Ampure XP beads, and was loaded on a Labchip platform to identify the size of ligation product. The results are shown in Table 11 and FIG. 11.

TABLE 11

| No. | Item | Molar concentration (pmol/mL) | % |
|---|---|---|---|
| 1 | Low marker | / | / |
| 2 | 200-bp PCR product | 6.44 | 61.86% |
| 3 | Product with one adapter | 2.38 | 22.86% |
| 4 | Product with two adapters | 0.98 | 9.41% |
| 5 | Polymers with adapter | 0.61 | 5.86% |
| 6 | Up marker | / | / |
| / | Effective library | 3.97 | 38.14% |
| / | Total | 10.41 | |

Comparative Example 2

The method for ligation of the embodiment adopts a one-step process as follows:

15 ng of 200-bp PCR product, 2 µL of 10×T4 ligase buffer, 2 µL of 1 µM adapter mix (adapter; the molar ratio of DNA to adapter was 1:17.6), 1 µL of T4 PNK and 2 µL of T4 DNA ligase were mixed in a 200-µL PCR tube. The mixture was diluted to 20 µL using water, well mixed, and incubated for 1 h at 16° C. to give the ligation product.

Figure 12:
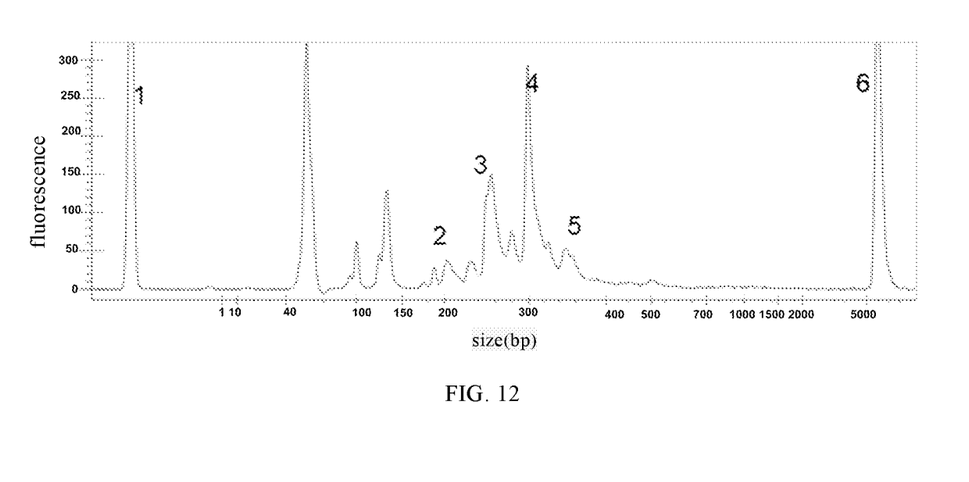
FIG. 12 is a diagram showing the results of identifying the size of ligation product by Labchip in Comparative Example 2.

The resulting mixture was purified using 0.8× Ampure XP beads, and was loaded on a Labchip platform to identify the size of ligation product. The results are shown in Table 12 and FIG. 12.

TABLE 12

| No. | Item | Molar concentration (pmol/mL) | % |
|---|---|---|---|
| 1 | Low marker | / | / |
| 2 | 200-bp PCR product | 0.76 | 11.71% |
| 3 | Product with one adapter | 2.25 | 40.83% |
| 4 | Product with two adapters | 2.07 | 34.98% |
| 5 | Polymers with adapter | 0.71 | 12.48% |
| 6 | Up marker | / | |
| / | Effective library | 5.03 | 77.5% |
| / | Total | 6.49 | |

The results of Comparative Examples 1 and 2 show that in a ligation reaction system without T4 RNA ligase I, the ligation efficiency is significantly reduced: in the two-step ligation process, the ligation efficiency was 38.14%, while in the one-step ligation reaction, the ligation efficiency was 77.5%.

The above results indicate that the method of Examples 1 to 10, in which T4 RNA Ligase I (T4 RNA ligase I) commonly used for the ligation between RNAs was added to the ligation of double-stranded DNA and the adapter, demonstrated a 85% or higher ligation efficiency of the double-stranded DNA fragment and the adapter and a high yield of effective library. The method for ligation requires no PCR process, and is convenient and cost-efficient.

Examples 2 to 10 adopt a one-step ligation process, which is easy to operate and is similar to the two-step process of Example 1 in efficiency.

Example 6, in which the molar ratio of DNA to adapter was 1:10, shows less adapter residue as compared with Examples 1 to 5.

Examples 7 to 9 show that at reduced doses of T4 RNA ligase I and T4 DNA ligase, the ligation efficiency is equivalent to that of the original doses. With reduced amount of enzymes used in the experiment, the cost can be reduced.

In Example 10, when the system was scaled up to adapting the sample concentration, the reaction efficiency of the method for ligation of the present disclosure showed no significant reduction.

The above examples only illustrate one or more embodiments of the present disclosure for the purpose of specific and detailed description, but should not be construed as limiting the scope of the present disclosure. It should be noted that various changes and modifications can be made by those skilled in the art without departing from the spirit of the present disclosure, and these changes and modifications are all within the scope of the present disclosure. Therefore, the protection scope of the present disclosure should be determined with reference to the appended claims.

The invention claimed is:

1. A method for nucleic acid fragment ligation, comprising ligating a first nucleic acid fragment and a second nucleic acid fragment in a mixed enzyme reaction system comprising a T4 DNA ligase, a T4 RNA ligase, and a T4 polynucleotide kinase,
   wherein the first nucleic acid fragment, the second nucleic acid fragment, the T4 DNA ligase, the T4 RNA ligase, and the T4 polynucleotide kinase are mixed for 20-40 minutes at 10-20° C. to obtain a ligation product, wherein the first nucleic acid fragment is a double-stranded DNA, and
   wherein the final concentration of the T4 RNA ligase in the ligation reaction system is 0.15 U/μL to 1 U/μL.

2. The method as claimed in claim 1, wherein the second nucleic acid fragment is a double-stranded nucleic acid fragment.

3. The method as claimed in claim 2, wherein the molar ratio of the first nucleic acid fragment to the second nucleic acid fragment is 1:8 to 1:20.

4. The method as claimed in claim 3, wherein the molar ratio of the first nucleic acid fragment to the second nucleic acid fragment is 1:10.

5. A method for constructing a sequencing library, comprising acquiring a ligation product by the method as claimed in claim 1, to obtain the sequencing library, wherein the first nucleic acid fragment is from a sample under test.

6. A sequencing method, comprising: acquiring a sequencing library using the method as claimed in claim 5, and sequencing the sequencing library.

7. The method as claimed in claim 2, wherein the second nucleic acid fragment comprises sequences of SEQ ID NOS.1 and 2, and SEQ ID NOS.3 and 4.

8. The method as claimed in claim 7, wherein SEQ ID NO. 1 has a modified amino group at the 5' end, SEQ ID NO. 2 has a modified phosphate group at the 5' end, SEQ ID NO. 3 has a modified amino group at the 5' end, and SEQ ID NO. 4 has a modified phosphate group at the 5' end.

9. The method as claimed in claim 7, wherein SEQ ID NOS.1 and 2, and SEQ ID NOS.3 and 4 are in a molar ratio of 1:1.

10. The method as claimed in claim 3, wherein formula (I) is used to calculate the amount of the first nucleic acid fragment:

$$pmols = \frac{m*10^3}{660*L}, \tag{I}$$

wherein m is the weight of the first nucleic acid fragment, in ng,

L is the length of the first nucleic acid fragment, in bp; and formula (II) is used to calculate the amount of the second nucleic acid fragment:

$$pmols = C*V \tag{II, wherein}$$

C is molar concentration of the second nucleic acid fragment, in μM,

V is volume of the second nucleic acid fragment, in μL.

\* \* \* \* \*

SEQUENCE LISTING

<160> NUMBER OF SEQ ID NOS: 4

<210> SEQ ID NO 1
<211> LENGTH: 51
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(51)
<223> OTHER INFORMATION: adapter

<400> SEQUENCE: 1
tccttgatac ctgcgaccat ccagttccac tcagatgtgt ataagagaca g     51

<210> SEQ ID NO 2
<211> LENGTH: 51
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(51)
<223> OTHER INFORMATION: adapter

<400> SEQUENCE: 2
ctgtctctta tacacatctg agtggaactg gatggtcgca ggtatcaagg a     51

<210> SEQ ID NO 3
<211> LENGTH: 50
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(50)
<223> OTHER INFORMATION: adapter

<400> SEQUENCE: 3
ctcagatcct acaacgacgc tctaccgatg aagatgtgta taagagacag     50

<210> SEQ ID NO 4
<211> LENGTH: 50
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(50)
<223> OTHER INFORMATION: adapter

<400> SEQUENCE: 4
ctgtctctta tacacatctt catcggtaga gcgtcgttgt aggatctgag     50